United States Patent
Musa

(10) Patent No.: US 6,570,032 B1
(45) Date of Patent: May 27, 2003

(54) COMPOUNDS CONTAINING VINYL SILANE AND ELECTRON DONOR OR ACCEPTOR FUNCTIONALITY

(75) Inventor: Osama M. Musa, Hillsborough, NJ (US)

(73) Assignee: National Starch and Chemical Investment Holding Corporation, New Castle, DE (US)

( * ) Notice: Subject to any disclaimer, the term of this patent is extended or adjusted under 35 U.S.C. 154(b) by 0 days.

(21) Appl. No.: 09/966,448

(22) Filed: Sep. 28, 2001

(51) Int. Cl.⁷ .................................................. C07F 7/08
(52) U.S. Cl. ....................... 556/465; 556/443; 556/445; 556/482; 556/489
(58) Field of Search ................................ 556/465, 482, 556/489, 443, 445

(56) References Cited

U.S. PATENT DOCUMENTS

| | | | | |
|---|---|---|---|---|
| 3,770,768 A | | 11/1973 | Holub et al. ............. 260/326 R |
| 3,803,196 A | | 4/1974 | Holub et al. ......... 260/448.2 N |
| 4,299,713 A | * | 11/1981 | Maringer et al. ..... 174/110 SR |
| 4,708,947 A | * | 11/1987 | Maruyama et al. ......... 503/209 |
| 4,722,975 A | * | 2/1988 | Itoh et al. .................... 525/288 |
| 4,814,475 A | * | 3/1989 | Funahashi et al. ........... 556/489 |
| 5,077,362 A | * | 12/1991 | Watanabe et al. ........... 526/255 |

OTHER PUBLICATIONS

Mayuzumi et al., The Synthesis of the silane coupling agent which has a Methacrylic base, Journal of Advanced Science, 9 (1&2), p. 157–158, Jun. 1997.*

Young et al., Silicon–tethered Heck reaction, Tetrahedron Letters, 42, p. 203–206, Jan. 2001.*

Ready, Thomas E.: "Facile and Effective Synthesis of Siloxane–Based Polyamines"; Macromol. Rapid Commun. 2001, 22, 654–657.

Search Results ACS Registry—(9 Pages).

Search Results ACS Registry—(12 Pages).

* cited by examiner

*Primary Examiner*—Robert Dawson
*Assistant Examiner*—Jeffrey B. Robertson
(74) *Attorney, Agent, or Firm*—Jane E. Gennaro

(57) ABSTRACT

Compounds containing vinyl silane and electron donor or electron acceptor functionality can be used as adhesion promoters or as the main resin in curable compositions.

5 Claims, No Drawings

US 6,570,032 B1

COMPOUNDS CONTAINING VINYL SILANE AND ELECTRON DONOR OR ACCEPTOR FUNCTIONALITY

FIELD OF THE INVENTION

This invention relates to compounds that contain vinyl silane and electron donor or electron acceptor functionality that can be used as adhesion promoters or curable compositions.

BACKGROUND OF THE INVENTION

Adhesive composition s are used in the fabrication n an assembly of semiconductor packages and microelectronic devices, such as in the bonding of integrated circuit chips to lead frames or other substrates, and the bonding of circuit packages or assemblies to printed wire boards. Lead frames can be fabricated of 42Fe/58Ni alloy (Alloy 42), copper, or silver- or palladium-coated copper, and wire boards of ceramic or laminate, and adhesives that in general have good performance may be deficient when used on one or more of these substrates.

The addition of adhesion promoters to the adhesive compositions or the use of curable resins that contain adhesion promoting capability as the adhesive would serve to correct this deficiency.

SUMMARY OF THE INVENTION

This invention relates to compounds that contain both vinyl silane functionality and electron donor or electron acceptor functionality. In another embodiment, this invention is an adhesive, coating, or encapsulant composition containing the inventive compounds.

DETAILED DESCRIPTION OF THE INVENTION

In one embodiment, this invention is a compound having the structure $$[(E)_q\text{—}R\text{—}X]_m\text{—}Si\text{—}[X'\text{—}R^1\text{—}(E')_q]_n$$
$$(R^2)_p$$

in which m and n independently are 0, 1, 2, or 3, but cannot both be 0, q is 1 or 2;
is 0, 1, or 2; X and X' independently are —O—, —N(H)—, or —N—Si—

R and $R^1$ independently are an alkyl, cycloalkyl, or aromatic group; $R^2$ is a vinyl, alkyl, cycloalkyl or aromatic group (which may be contained within a small molecular entity, oligomer or polymer); and E and E' are independently an electron donor or electron acceptor.

Suitable electron acceptor groups are, for example, maleimides, acrylates, fumarates and maleates. Suitable electron donor groups are, for example, vinyl ethers, vinyl silanes, and carbon to carbon double bonds external to an aromatic ring and conjugated with the unsaturation in the aromatic ring, such as styrenic and cinnamyl groups.

In another embodiment, this invention is a curable composition, such as an adhesive, coating, or encapsulan, containing the inventive vinyl silane compounds. The composition can be in paste form prepared by milling or blending the components, or in film form, made by film making techniques known to those skilled in the art. The curable composition will include optionally a curing agent, and optionally a filler.

The vinyl silane compounds can be the main component in the curable composition or can be added as an adhesion promoter to another curable resin. When used as an adhesion promoter, the amount of the vinyl silane compound used in the curable composition will be an effective amount to promote adhesion and, in general, an effective amount will range from 0.005 to 20.0 percent by weight of the formulation, Examples of curable resins for use as the main component other than the inventive vinyl silanes include epoxies, electron donor resins (for example, vinyl ethers, thiol-enes, and resins that contain carbon to carbon double bonds attached to an aromatic ring and conjugated with the unsaturation in the aromatic ring, such as compounds derived from cinnamyl and styrenic starting compounds), and electron acceptor resins (for example, fumarates, maleates, acrylates, and maleimides).

Suitable curing agents are thermal initiators and photo-initiators present in an effective amount to cure the composition. In general, those amounts will range from 0.5% to 30%, preferably 1% to 20%, by weight of the total organic material (that is, excluding any inorganic fillers) in the composition. Preferred thermal initiators include peroxides, such as butyl peroctoates and dicumyl peroxide, and azo compounds, such as 2,2'-azobis(2-methyl-propanenitrile) and 2,2'-azobis(2-methyl-butanenitrile). A preferred series of photoinitiators is one sold under the trademark Irgacure by Ciba Specialty Chemicals. In some formulations, both thermal initiation and photoinitiation may be desirable: the curing process can be started either by irradiation, followed by heat, or can be started by heat, followed by irradiation. In general, the curable compositions will cure within a temperature range of 70° C. to 250° C., and curing will be effected within a range of ten seconds to three hours. The actual cure profile will vary with the components and can be determined without undue experimentation by the practitioner.

The formulations may also comprise thermally or electrically conductive or nonconductive fillers, Suitable conductive fillers are carbon black, graphite, gold, silver, copper, platinum, palladium, nickel, aluminum, silicon carbide, boron nitride, diamond, and alumina. Suitable nonconductive fillers are particles of vermiculite, mica, wollastonite, calcium carbonate, titania, sand, glass, fused silica, fumed silica, barium sulfate, and halogenated ethylene polymers, such as tetrafluoroethylene, trifluoroethylene, vinylidene fluoride, vinyl fluoride, vinylidene chloride, and vinyl chloride. If present, fillers generally will be in amounts of 20% to 90% by weight of the formulation.

The following are the Synthetic Procedures used to make the vinyl silane compounds disclosed in this specification, Examples of the vinyl silane compounds and performance in curable compositions.

SYNTHETIC PROCEDURES

PROCEDURE 1. Reaction of alcohol or amine with vinyl silane. One mole equivalent of alcohol or amine and triethylamine are mixed in dry toluene at 0° C., to which is added one mole equivalent of vinyl silane dissolved in toluene. The mixture is allowed to react for four hours at room temperature, after which the solvent is evaporated to give the product.

PROCEDURE 2. Reaction of phenol or acetoacetate with alkyl or alkenyl halide. One mole equivalent of phenol or acetoacetate is charged to a three-necked flask equipped with a mechanical stirrer, condenser, and inlet/outlet tube for nitrogen. Methyl ethyl ketone is added and the reaction placed under nitrogen gas. Alkyl or alkenyl halide is added through a syringe and stirring initiated. Potassium carbonate is added and the reaction mixture heated at 50° C. for 11 hours, allowed to cool to room temperature, and vacuum filtered. The filtrate is washed with 5% NaOH and 10% $Na_2SO_4$. The organic layer is dried over $MgSO_4$, and the solvent evaporated off to give the product.

PROCEDURE 3. Reaction of isocyanate with amine. One mole equivalent of isocyanate is solvated in toluene in a three-necked flask equipped with a mechanical stirrer, addition funnel and nitrogen inlet/outlet. The reaction is placed under nitrogen and the solution heated to 60° C. The addition funnel is charged with one mole equivalent of amine in toluene, and this solution is added to the isocyanate solution over ten minutes. The resulting mixture is heated for an additional three hours at 60° C., after which it is allowed to cool to room temperature. The solvent is removed in vacuo to give the product.

PROCEDURE 4. Reaction of isocyanate with alcohol. One mole equivalent of isocyanate is solvated in toluene in a three-necked flask equipped with a mechanical stirrer, addition funnel and nitrogen inlet/outlet. The reaction is placed under nitrogen and catalytic of dibutyltin dilaurate is added with stirring as the solution is heated to 60° C. The addition funnel is charged with one mole equivalent of alcohol dissolved in toluene. This solution is added to the isocyanate solution over ten minutes, and the resulting mixture is heated for an additional three hours at 60° C. After the reaction is allowed to cool to room temperature, the solvent is removed in vacuo to give the product.

PROCEDURE 5. Reaction of alkyl halide with amine or mercaptan. One mole equivalent of alkyl halide is solvated in THF in a three neck flask equipped with a mechanical stirrer and addition funnel. The addition funnel is charged with one mole equivalent of amine or mercaptan in THF and this solution is added to the alkyl halide solution over ten minutes at 0° C. The resulting mixture is stirred for 12 hours at room temperature, after which the solvent is removed in vacuo and ether and water are added to the resulting material. The organic layer is extracted and dried over $MgSO_4$, and the solvent removed in vacuo to give the product.

EXAMPLES

Example 1

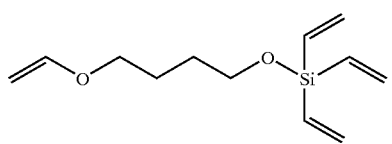

To a 250 mL round bottle flask was added 1,4-butanediol vinyl ether (8.03 g, 0.07 mole), triethylamine (6.98 g, 0.07 mole), and toluene (50 mL). Trivinyl chlorosilane (10.00 g, 0.07 mole) was added dropwise at 0° C. (performed in an ice bath) through a slow-add funnel. Once addition was completed, the ice bath was removed and the mixture was stirred at room temperature for four hours. The mixture was filtered and the filtrate charged to a 250 mL round bottle flask. The solvent was removed under reduced pressure to give the product in 89% yield.

Example 2

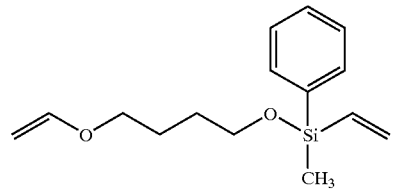

To a 250 mL round bottle flask was added 1,4-butanediol vinyl ether (7.69 g, 0.07 mole), triethylamine (6.67 g, 0.07 mole) and toluene (50 mL). Vinyl phenyl methyl chlorosilane (12.10 g, 0.07 mole) was added dropwise at 0° C. (performed in an ice bath) through a slow-add funnel. Once addition was completed, the ice bath was removed and the mixture was stirred at room temperature for four hours. The mixture was filtered and the filtrate charged to a 250 mL round bottle flask. The solvent was removed under reduced pressure to give the product in 90% yield.

Example 3

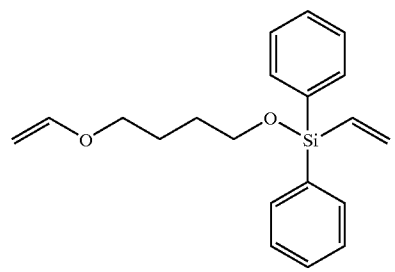

To a 250 mL round bottle flask was added 1,4-butanediol vinyl ether (9.49 g, 0.082 mole), triethylamine (8.25 g, 0.082 mole) and toluene (50 mL). Diphenyl vinyl chlorosilane (20.0 g, 0.082 mole) was added dropwise at 0° C. (performed in an ice bath) through a slow-add funnel. Once addition was completed, the ice bath was removed and the mixture was stirred at room temperature for four hours. The mixture was filtered and the filtrate charged to a 250 mL round bottle flask. The solvent was removed under reduced pressure to give the product in 86% yield.

Example 4

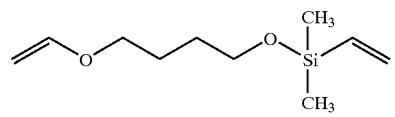

This compound is prepared according to Procedure 1 by the reaction of 1,4-butanediol vinyl ether with dimethyl vinyl chlorosilane.

Example 5

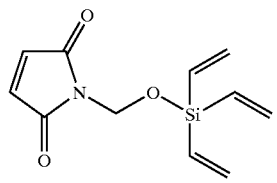

This compound is prepared according to Procedure 1 by the reaction of trivinyl chlorosilane with N-methylolmaleimide (prepared according to J. Bartus, W. L. Simonsick, and O. Vogl, *J.M.S.-Pure Appl. Chem.*, A36 (3), 355, 1999.

Example 6

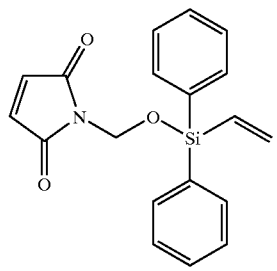

This compound is prepared according to Procedure 1 by the reaction of diphenyl vinyl chlorosilane with N-methylolmaleimide (prepared according to J. Bartus, W. L. Simonsick, and O. Vogl, *J.M.S.-Pure Appl. Chem.*, A36 (3), 355, 1999.

Example 7

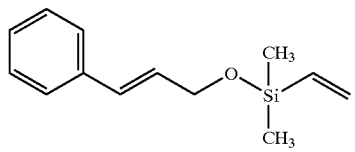

This compound is prepared according to Procedure 1 by the reaction of cinnamyl alcohol with dimethyl vinyl chlorosilane.

Example 8

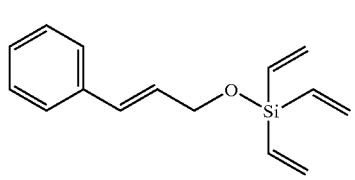

This compound is prepared according to Procedure 1 by the reaction of cinnamyl alcohol with trivinyl chlorosilane.

Example 9

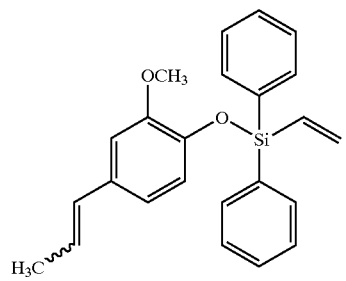

This compound is prepared according to Procedure 1 by the reaction of isoeugenol with diphenyl vinyl chlorosilane.

Example 10

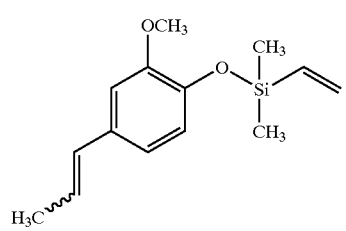

This compound is prepared according to Procedure 1 by the reaction of isoeugenol with dimethyl vinyl chlorosilane.

Example 11

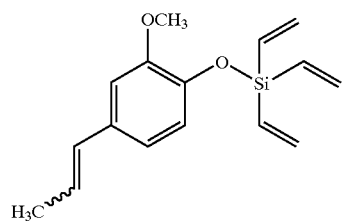

This compound is prepared according to Procedure 1 by the reaction of isoeugenol with trivinyl chlorosilane.

Example 12

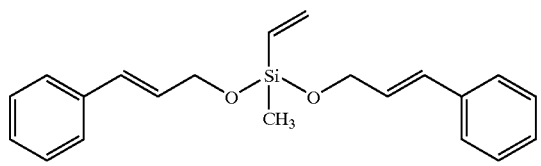

This compound is prepared according to Procedure 1 by the reaction of cinnamyl alcohol with methyl vinyl dichlorosilane.

Example 13

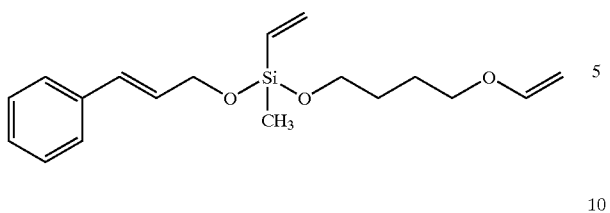

This compound is prepared according to Procedure 1 by the reaction of cinnamyl alcohol with methyl vinyl dichlorosilane, followed by reaction with 1,4-butanediol vinyl ether according to Procedure 1.

Example 14

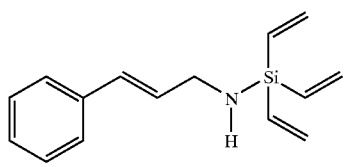

This compound is prepared according to Procedure 1 by the reaction one molar equivalent of cinnamyl amine with one molar equivalent of trivinyl chlorosilane.

Example 15

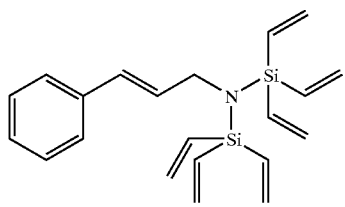

This compound is prepared according to Procedure 1 by the reaction of one molar equivalent of cinnamyl amine with two molar equivalent of trivinyl chlorosilane.

Example 16

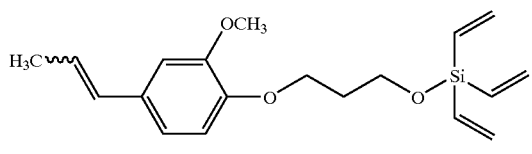

This compound is prepared according to Procedure 2 by the reaction of isoeugenol with 1-bromo propanol, followed by reaction with trivinyl chlorosilane according to Procedure 1.

Example 17

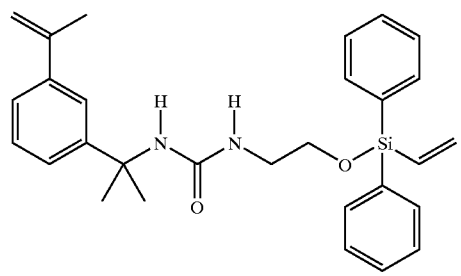

This compound is prepared according to Procedure 3 by the reaction of m-TMI with ethanol amine, followed by reaction with diphenyl vinyl chlorosilane according to Procedure 1.

Example 18

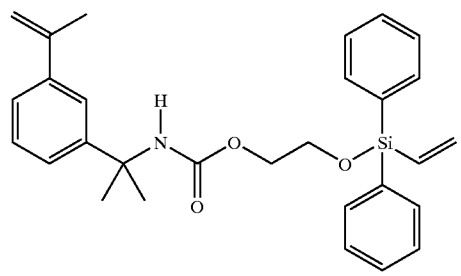

This compound is prepared according to Procedure 4 by the reaction of m-TMI with ethylene glycol, followed by reaction with diphenyl vinyl chlorosilane according to Procedure 1.

Example 19

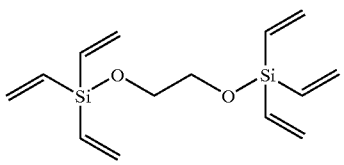

This compound is prepared according to Procedure 1 by the reaction of ethylene glycol with trivinyl chlorosilane.

Example 20

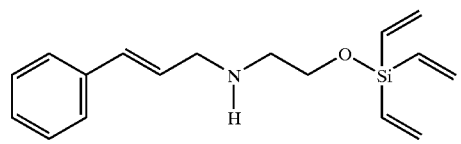

This compound is prepared according to Procedure 3 by the reaction of cinnamyl bromide with ethanol amine, followed by reaction with one molar equivalent of trivinyl chlorosilane according to Procedure 1.

Example 21

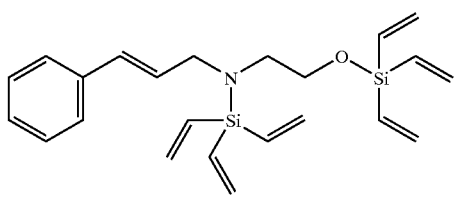

This compound is prepared according to Procedure 5 by the reaction of cinnamyl bromide with ethanol amine, followed by reaction with two molar equivalents of trivinyl chlorosilane according to Procedure 1.

Example 22

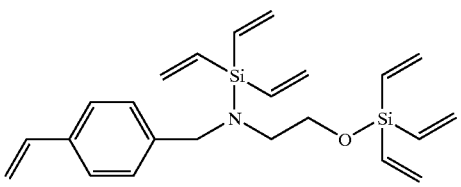

This compound is prepared according to Procedure 5 by the reaction of 4-vinyl benzyl chloride with ethanol amine, followed by reaction with two molar equivalents of trivinyl chlorosilane according to Procedure 1.

Example 23

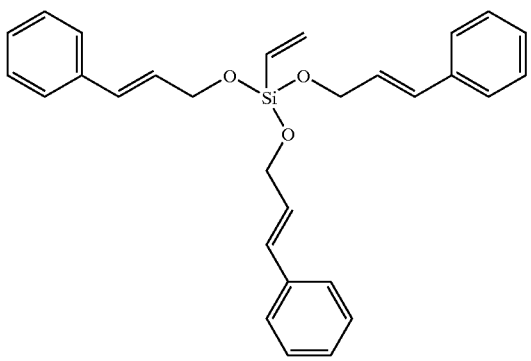

This compound is prepared according to the Procedure 1 by the reaction of cinnamyl alcohol with vinyltrichlorosilane.

Example 24

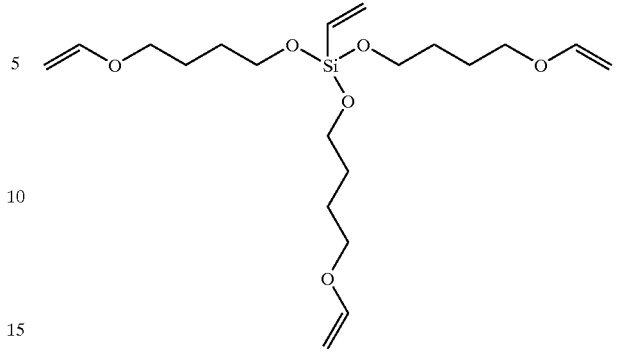

This compound is prepared according to the Procedure 1 by the reaction of 1,4-butanediol vinyl ether with vinyltrichlorosilane.

Example 25

Performance data. An adhesive formulation was prepared comprising a bismaleimide, a compound with cinnamyl functionality, an epoxy, curing agents, and 75% by weight silver. Vinyl silane compounds (including a commercially available material as a control) and the compounds from Examples 1, 2, and 3 were added to this composition at 1 weight % and the individual compositions tested for adhesive strength as die attach adhesives.

The adhesive was dispensed on a silver coated leadframe with a die pad, 650×650 mil. A silicon die, 500×500 mil, was placed onto the adhesive and the adhesive cured in an oven at 175° C. for 30 minutes. The cured assemblies were then subjected to 85° C./85% relative humidity for 48 hours, after which the die was sheared from the leadframe at 90 degrees with a Dage 2400-PC Die Shear Tester at 250° C.

Ten assemblies for each adhesive composition were tested and the average given in Kilogram force as the result. The results are set out in the following table and show that the addition of the inventive compounds gives improved, or at least comparable, adhesive strength to a vinyl silane commercially available (from Gelest, Inc., SID-4608) in a curable composition under the above conditions.

| VINYL SILANE | DIE SHEAR STRENGTH KgF |
| --- | --- |
| None | 20.1 |
| SID-4608 | 28.6 |
| Compound from Ex. 1 | 36.0 |
| Compound from Ex. 2 | 30.3 |
| Compound from Ex. 3 | 33.5 |

What is claimed:

1. A compound having the structure:

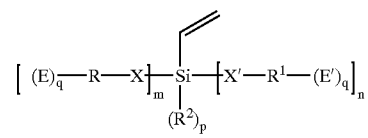

in which m and n independently are 0, 1, or 2, but cannot both be 0;

q is 1 or 2;

p is 0, 1, or 2;

X and X' independently are

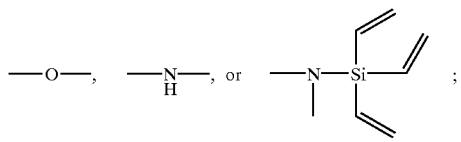

R and R¹ independently are an alkyl, cycloalkyl, or aromatic group;

R² is a vinyl, alkyl, cycloalkyl or aromatic group; and

E and E' are selected from the group consisting of maleimide, fumarate, maleate, vinyl ether, styrenic, and vinyl silane groups.

2. The compound according to claim 1 in which n is 0; m and q are 1; p is 2; X is oxygen; R² is vinyl, alkyl, or aromatic; R is alkyl; and E is vinyl ether.

3. The compound according to claim 1 having the structure:

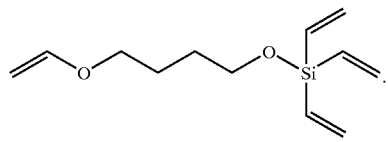

4. The compound according to claim 1 having the structure:

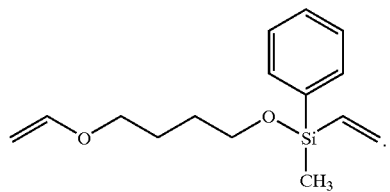

5. The compound according to claim 1 having the structure:

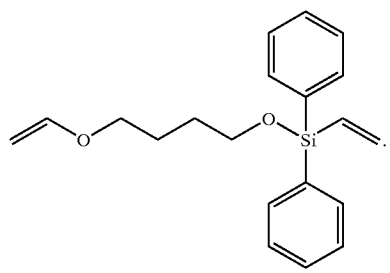

* * * * *